(12) United States Patent
Bierman

(10) Patent No.: US 6,796,310 B2
(45) Date of Patent: Sep. 28, 2004

(54) ENDO-TRACHEAL TUBE SECUREMENT SYSTEM

(75) Inventor: Steven F. Bierman, Del Mar, CA (US)

(73) Assignee: Venetec International, Inc., San Diego, CA (US)

( * ) Notice: Subject to any disclaimer, the term of this patent is extended or adjusted under 35 U.S.C. 154(b) by 77 days.

(21) Appl. No.: 10/270,883

(22) Filed: Oct. 11, 2002

(65) Prior Publication Data

US 2003/0089374 A1 May 15, 2003

Related U.S. Application Data

(60) Provisional application No. 60/328,727, filed on Oct. 11, 2001.

(51) Int. Cl.[7] .............................................. A61M 16/00
(52) U.S. Cl. ............................ 128/207.17; 128/207.11; 128/206.27; 128/DIG. 26; 128/202.18
(58) Field of Search .................... 128/DIG. 26, 202.18, 128/207.11, 857, 866, 845, 202.29, 202.28, 203.11, 911, 912, 202.27, 908, 206.27, 207.29, 207.17; 602/17, 18, 74; 601/40–44; 600/21, 22; 5/636–639

(56) References Cited

U.S. PATENT DOCUMENTS

| | | | |
|---|---|---|---|
| 3,046,989 A | | 7/1962 | Hill |
| 3,461,858 A | * | 8/1969 | Michelson ................... 601/41 |
| 3,482,571 A | | 12/1969 | Behrendt |
| 3,602,227 A | | 8/1971 | Andrew |
| 4,142,527 A | | 3/1979 | Garcia |
| 4,182,322 A | * | 1/1980 | Miller ............................ 5/637 |
| 4,284,076 A | | 8/1981 | Hall |
| 4,297,999 A | * | 11/1981 | Kitrell ................... 128/205.16 |
| 4,310,307 A | * | 1/1982 | Bellisario .................... 433/33 |
| 4,331,143 A | | 5/1982 | Foster |
| 4,449,527 A | | 5/1984 | Hinton |
| 4,548,200 A | | 10/1985 | Wapner |
| 4,592,351 A | | 6/1986 | Smith et al. |
| 4,658,814 A | | 4/1987 | Anderson |
| 4,683,882 A | | 8/1987 | Laird |
| 4,744,358 A | | 5/1988 | McGinnis |
| 4,774,944 A | | 10/1988 | Mischinski |
| 4,821,736 A | | 4/1989 | Watson |
| 4,832,019 A | | 5/1989 | Weinstein et al. |
| 4,850,348 A | | 7/1989 | Pell et al. |
| 4,867,154 A | | 9/1989 | Potter et al. |
| 4,906,234 A | | 3/1990 | Voychehovski |
| 4,932,943 A | | 6/1990 | Nowak |
| 4,988,062 A | * | 1/1991 | London ..................... 248/68.1 |
| 5,007,122 A | * | 4/1991 | Daughdrill ..................... 5/637 |
| 5,009,227 A | | 4/1991 | Nieuwstad |
| 5,038,778 A | | 8/1991 | Lott |
| 5,042,477 A | | 8/1991 | Lewis |
| 5,069,206 A | | 12/1991 | Crosbie |
| 5,076,269 A | | 12/1991 | Austin |

(List continued on next page.)

Primary Examiner—Aaron J. Lewis
Assistant Examiner—Mital Patel
(74) Attorney, Agent, or Firm—Knobbe Martens Olson & Bear LLP

(57) ABSTRACT

A system for securing an endo-tracheal or other tube in position upon a patient includes a head pad and securing members which can be adjustably attached to the head pad. The head pad is configured to support the head of a patient in a supine position. The head pad includes a number of slits formed in each lateral side of the head pad, such that a securing member can be threaded through any one of the slits. The securing member is configured to be releasably and adjustably attachable to the lateral sides of the head pad by being secured to itself via hook and, loop fastener portions disposed upon the member. The opposite end of the securement member can include an adhesive layer or other mechanism for attachment of the end of the member to the endo-tracheal tube or other medical article.

17 Claims, 11 Drawing Sheets

U.S. PATENT DOCUMENTS

| | | | |
|---|---|---|---|
| 5,205,832 A | | 4/1993 | Tuman |
| 5,237,988 A | | 8/1993 | McNeese |
| 5,253,643 A | | 10/1993 | Price |
| 5,295,480 A | | 3/1994 | Zemo |
| 5,305,742 A | | 4/1994 | Styers et al. |
| 5,320,097 A | | 6/1994 | Clemens et al. |
| 5,345,931 A | | 9/1994 | Battaglia, Jr. |
| 5,357,952 A | | 10/1994 | Schuster et al. |
| 5,368,024 A | | 11/1994 | Jones |
| 5,383,451 A | | 1/1995 | DeIulio |
| 5,387,177 A | * | 2/1995 | Dunn ..................... 600/22 |
| 5,398,679 A | | 3/1995 | Freed |
| 5,402,776 A | | 4/1995 | Islava |
| 5,411,484 A | | 5/1995 | Shattuck |
| 5,479,921 A | * | 1/1996 | Reif ..................... 128/207.17 |
| 5,488,944 A | * | 2/1996 | Kennedy ............... 128/202.18 |
| 5,507,285 A | | 4/1996 | Mota |
| 5,513,633 A | | 5/1996 | Islava |
| 5,515,867 A | | 5/1996 | Lamb |
| 5,531,229 A | | 7/1996 | Dean et al. |
| 5,551,421 A | | 9/1996 | Noureldin et al. |
| 5,555,881 A | | 9/1996 | Rogers et al. |
| 5,558,090 A | | 9/1996 | James |
| 5,649,534 A | | 7/1997 | Briggs, II |
| 5,653,232 A | | 8/1997 | Rogers et al. |
| 5,672,159 A | | 9/1997 | Warrick |
| 5,743,885 A | | 4/1998 | Hoerby |
| 5,771,513 A | | 6/1998 | Kirchgeorg et al. |
| 5,803,079 A | | 9/1998 | Rogers et al. |
| 5,806,516 A | | 9/1998 | Beattie |
| 5,829,430 A | | 11/1998 | Islava |
| 5,918,599 A | | 7/1999 | Shesol |
| 5,924,421 A | | 7/1999 | Rosbrook et al. |
| 5,927,276 A | | 7/1999 | Rodriguez |
| 5,934,276 A | | 8/1999 | Fabro et al. |
| 5,967,144 A | * | 10/1999 | Reynolds ..................... 5/637 |
| 5,988,173 A | * | 11/1999 | Scruggs ..................... 128/870 |
| 6,009,872 A | | 1/2000 | Delaplane et al. |
| 6,029,668 A | | 2/2000 | Freed |
| 6,067,985 A | | 5/2000 | Islava |
| 6,336,457 B1 | | 1/2002 | Hudson et al. |

* cited by examiner

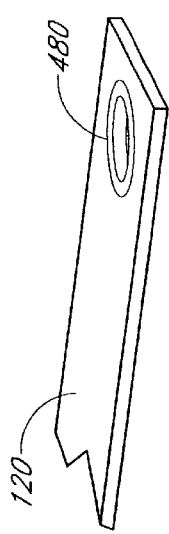
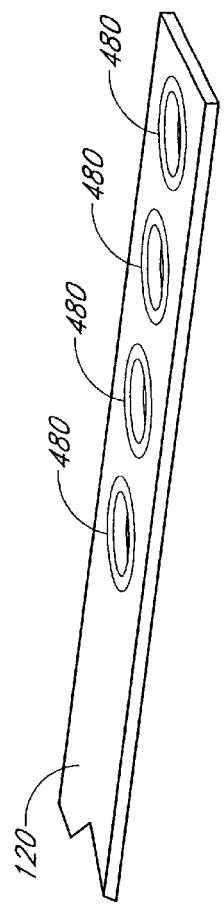
FIG. 14
FIG. 14A

ENDO-TRACHEAL TUBE SECUREMENT SYSTEM

This application claims priority benefit under 35 U.S.C. §119(e) from U.S. Provisional Application No. 60/328,727 entitled "ENDO-TRACHEAL TUBE SECUREMENT SYSTEM" filed on Oct. 11, 2001, which is hereby incorporated by reference herein in its entirety.

BACKGROUND OF THE INVENTION

1. Field of the Invention

This invention relates generally to techniques and systems for securing an endo-tracheal tube or other medical line to a patient. More specifically, this invention relates to an anchoring system and related techniques that maintain an endo-tracheal tube in position upon a patient and/or that prevent migration of the tube within the throat of the patient.

2. Description of the Related Art

When an endo-tracheal tube is used with a medical patient, it is common for the tube to be secured to the patient by means of adhesive tape. Failing to secure the endo-tracheal tube can result in the migration of the tube within the throat of the patient. Such motion is undesirable since outward motion of the tube can result in the tube moving entirely out of the airway of the patient, eliminating its effectiveness and potentially ventilating the patient's gastro-intestinal tract instead of the his lungs. Inward motion of the tube is undesirable because it will eventually result in the tube moving down one of the patient's bronchi, preventing air from being ventilated to the other lung. This will quickly lead to the collapse of the unventilated lung. Even slight back and forth motion of the tube within the throat can result in tracheomalacia and ultimately in the weakening or collapse of the trachea, which may require permanent stenting to maintain an open airway.

In order to avoid these undesirable consequences, it is common to secure the endo-tracheal tube in the proper position upon the patient. For instance, a medical practitioner may, after positioning the tube properly within the throat of the patient, wrap adhesive tape around the tube and tape it to the patient. Various devices are often used as adaptors for endo-tracheal tubes, and sometimes these devices are taped to the patient. Other techniques can involve the use of straps which are wrapped around the head of the patient and which connect to the tube, or to the adaptor of the tube.

Such arrangements present certain problems for a medical practitioner. One difficulty is that once secured, it is generally not convenient to release or adjust the securement of the endo-tracheal tube. For instance, if an adhesive is used to secure the tube to the patient, adjusting or resecuring the tube in such situations requires that the adhesive be removed from the patient and the tube, and then fresh adhesive be used to properly resecure the tube upon the patient. Such adhesive tape can be difficult to work with for medical practitioners wearing latex gloves, and contact with the adhesive can introduce tears or microscopic perforations into the gloves, compromising their effectiveness. Furthermore, repeated application and removal of adhesive from the face of a patient can irritate the skin of the patient.

Systems that use straps are often difficult to adjust and generally involve complex arrangements that can be difficult to position properly upon a patient. These systems can be difficult to remove from a patient as well. Furthermore, such systems for retaining an endo-tracheal tube in position often occlude the mouth of the patient. This can prevent a health-care worker from having access to the mouth to allow for mouth care, such as suction of fluid from the oral cavity.

Therefore, a need continues to exist for an improved system to secure an endo-tracheal tube to a medical patient.

SUMMARY OF THE INVENTION

One aspect of the system described herein is a securement device for maintaining an endo-tracheal or other medical tube in position upon the head of a patient. The device includes a head pad having a support and a platen. The platen is a generally flat rectangular member having a central region and a pair of securing regions, one of the pair of securing regions extending from each lateral side of the platen. Each securing region has a plurality of openings such as slits formed in it. The support can be attached to an upper surface of the central region of the platen such that the openings of the pair of securing regions are exposed to each lateral side of the support.

Another aspect of the securement device is a securing member. A plurality of securing members can be used with a single head pad. Each securing member comprises a flat elongated flexible strip having a first end and a second end. The first end of the member has a hook region upon which the hooks of a hook and loop fastener are disposed and also has a loop region upon which the loops of a hook and loop fastener are disposed. The second end of the member has a fastener configured to attach the member to the medical tube.

The members are configured to be attached to the head pad by passing the first end of the member through one of the slits of the head pad and then attaching the hook region of the member to the loop region of the member to secure the member to the head pad.

In one mode, the fastener of the second end of the securing member comprises an adhesive layer disposed upon one side of the second end of the securing member. This adhesive may be covered by a removable release liner.

In another mode, the fastener of the second end of the securing member comprises a hook configured to cooperate with an aperture of the endo-tracheal tube.

In yet another node, the fastener of the second end of the securing member comprises an aperture configured to be secured to a hook of the endo-tracheal tube. In further modes, a plurality of additional apertures can be disposed at different positions along the second end of the member.

In another aspect of the described system, the medical tube itself may include appropriate fastener elements such as hooks or apertures as described above.

In another aspect of the described system, an attachable fastener unit is used. The attachable fastener unit can be attached to the medical tube, and can comprise a support member and at least one second fastener element disposed upon the support member. The support member is configured to be attached to the medical article and the second fastener element is configured to cooperate with the fastener element on the second end of one of the securing members so as to attach the securing member to the attachable fastener unit.

In operation, the securement devices described herein may be used to secure a medical tube to the head of a patient. This can be done by placing the head of the patient upon the support of the head pad and positioning a medical tube upon the head of the patient. The secuing members can be attached to the medical tube via one of the techniques described above. Each of the securement members can be made snug between the head pad and the medical tube. This is done bypassing the first end of the member through one of the slits of the head pad and then attaching the hook region of the member to the loop region of the member in a position such that the member is taut.

Further aspects, features, and advantages of the present invention will become apparent from the detailed description of the preferred embodiments that follow.

BRIEF DESCRIPTION OF THE DRAWINGS

The invention will now be describe d with reference to the drawings summarized below. These drawings and the associated description are provided to illustrate a preferred embodiment of the invention, and not to limit the scope of the invention.

FIG. 14 illustrates a securing member for use with the adaptor of FIG. 13.

FIG. 14A illustrates another securing member suitable for use with the adaptor of FIG. 13.

DETAILED DESCRIPTION OF PREFERRED EMBODIMENTS

The following description and examples illustrate preferred embodiments of the present securement system disclosed in the context of use with an exemplary endo-tracheal tube. The principles of the present invention, however, are not limited to endo-tracheal tubes such as those shown. It will be understood by those of skill in the art in view of the present disclosure that the securement system described can be used with other types of medical articles, including, but not limited to: endo-tracheal tubes of different design, either with or without tube adaptors, naso-tracheal tubes, and the like. One skilled in the art may also find additional applications for the devices and systems disclosed herein. Thus, the illustration and description of the securement system in connection with an endo-tracheal tube is merely exemplary of one possible application of the securement system and technique disclosed.

Figure 1:
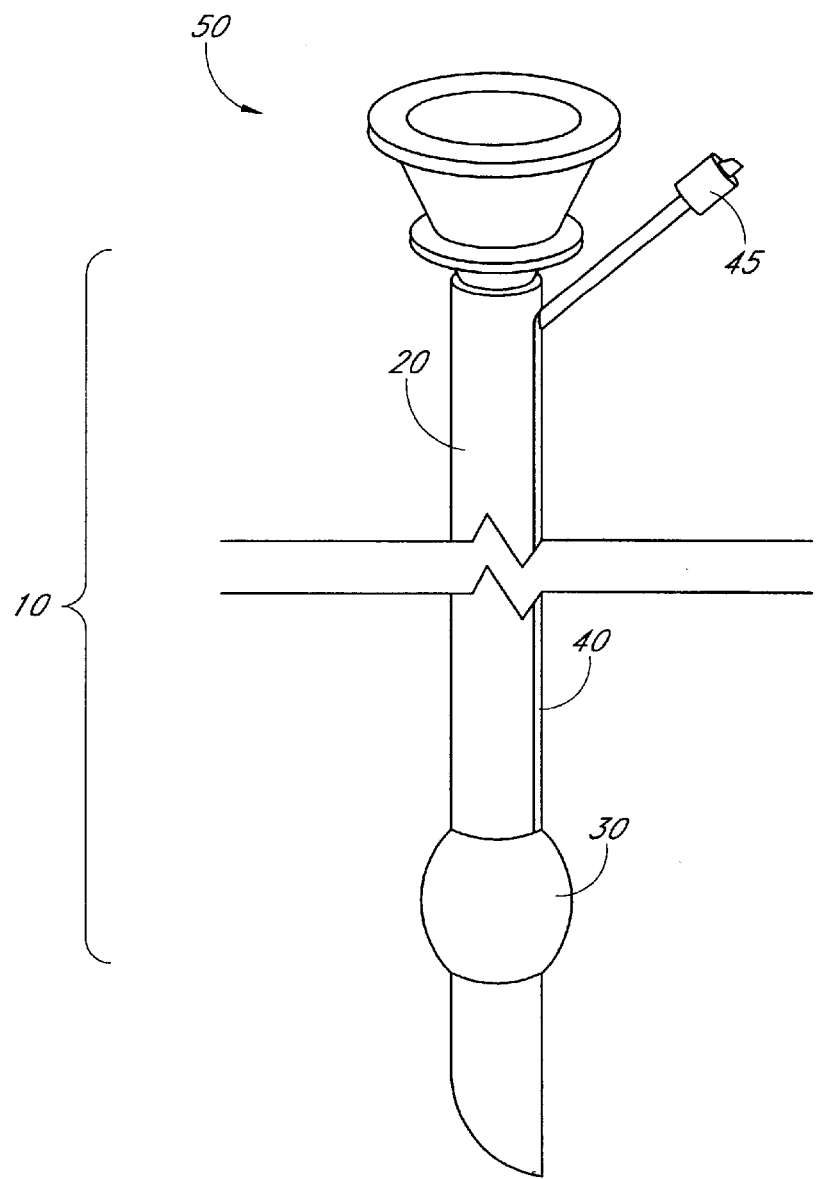
FIG. 1 illustrates an exemplary endo-tracheal tube and adaptor.

The exemplary endo-tracheal tube 10, as shown in FIG. 1, comprises an elongated tubular body 20 with a central lumen. The tube is inserted into the trachea of a medical patient, generally through the mouth. The endo-tracheal tube can include an inflatable balloon 30 located on the portion of the tube which is inserted into the throat. In order to provide the ability to inflate or deflate the balloon, a secondary inflation lumen 40 can extend from the balloon 30 portion of the tube along the tubular body 20 and can extend away from the tubular body at a location which will be located outside the patient at all times. A valve 45 is preferably disposed upon the end of this inflation lumen for use in controlling the inflation of the balloon.

As is shown, the endo-tracheal tube 10 can be used with an adaptor 50 which is disposed upon the external end of the endo-tracheal tube 10. This adaptor provides a connection between the lumen of the tube and any other tube or apparatus to which the endo-tracheal tube can be connected, such as a ventilator.

OVERVIEW

Figure 2:
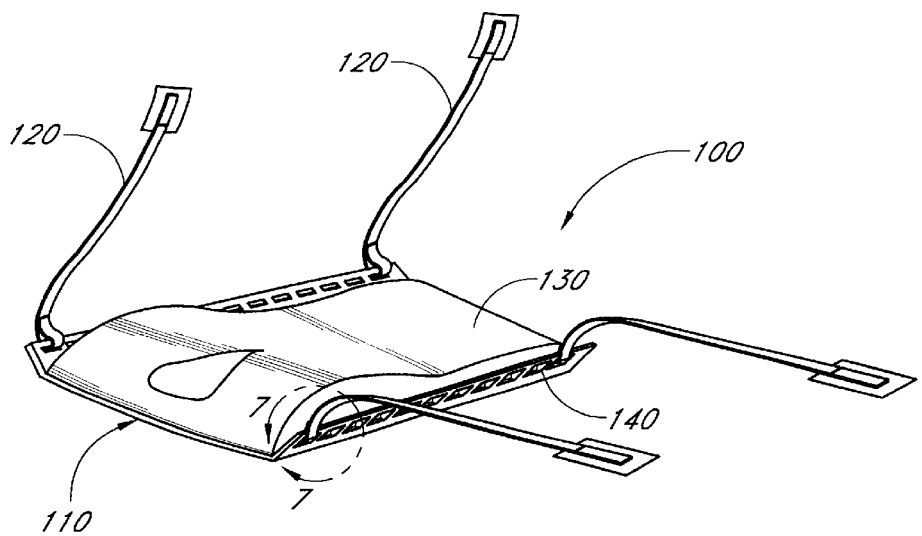
FIG. 2 illustrates one preferred embodiment of a securement system in accordance with the present invention.

As shown in FIG. 2, the securement system 100 described comprises a head pad 110 and one or more securing members 120. The head pad is designed to be placed underneath the head of the intubated patient. The head pad contains a head support 130 upon which the head and neck of the patient will rest. Disposed on each lateral side of the head pad are one or more slits 140 or holes through which one end of a securing member 120 can be inserted. In a preferred form, the head pad 110 includes a plurality of slits 140 and four securing members are attached to the head pad by inserting one end of each member through a slit upon the head pad, and then affixing them in position, for example via a hook and loop fastener arrangement (e.g., Velcro®) disposed upon the member. The free end of each securing member includes a mechanism to secure the member to the endo-tracheal tube or its adaptor. This can include an adhesive strip, a hook designed to attach to an eyelet upon the tube or adaptor, a clip component designed to engage a corresponding clip component (e.g., a receptacle) disposed on the endo-tracheal tube or adaptor, or such other fastener as is known to those of skill in the art. These will be discussed in greater detail below.

Once the patient is intubated and his head is placed upon the head pad 110, each of the four members 120 are attached to the tube 10 or tube adaptor 50. Once the members are attached, they are made snug by releasing their attachment to the head pad 110 and then resecuring the member 120 to the head pad after pulling the member taut. By this arrangement, a snug four-point securement can be made between the endo-tracheal tube 10 and the head pad 110, holding the tube in position upon the patient, and inhibiting undesirable migration of the tube within the throat of the patient. The system can easily be removed from the patient by releasing the members 120 from the head pad 110, allowing for quick release, as well as for readjustment of the positioning of the tube.

The above features will now be described in greater detail with reference to the included Figures.

HEAD PAD

Figure 3:
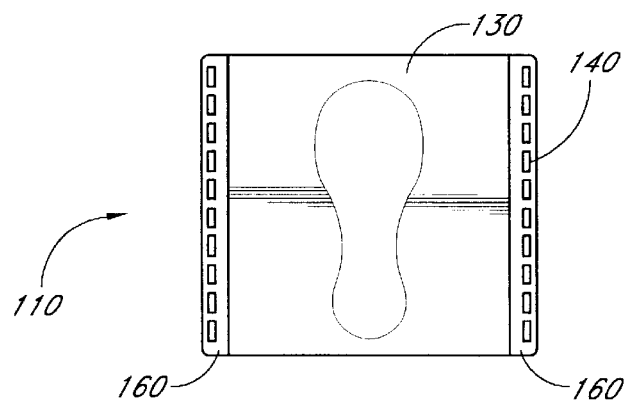
FIG. 3 illustrates a top view of the head pad of the securement system of FIG. 2.
Figure 4:
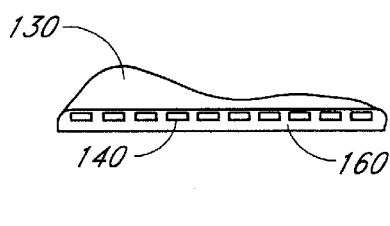
FIG. 4 illustrates a side view of the head pad of FIG. 3.
Figure 5:
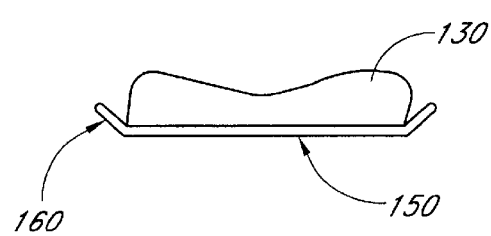
FIG. 5 illustrates a front view of the head pad of FIG. 3.

An exemplary head pad 110 for use in the described endo-tracheal tube securement system 100 is shown in FIGS. 3 to 5. The head pad 110 preferably comprises two main components, a head support 130 and a platen 150. For the illustrated head pad the platen 150 is a generally rectangular plastic piece, which forms the lower body of the head pad 110 and which is bent upwardly along two opposite edges to form the securing regions 160 to which the securing members 120 will be attached. As shown in FIG. 5, the securing regions 160 extend both laterally and upwardly from the central flat, rectangular portion of the platen. The platen is generally sized such that the central rectangular portion of the head pad will extend both beyond the crown and chin of a patient, as well as to each side of the patient's head.

Each securing region 160 has a plurality of slits 140 or holes disposed along the longitudinal length of the securing region. Each hole is sized so as to accept one end of a securing member 120. As used herein, the word "end" is not intended to be limited to the actual terminus of a particular member. "End" is used broadly to refer to not only the terminus of a particular structural element, but also the region of the element which is near this terminus. While the platen 150 can include as few as two slits on each securing region (for a total of four slits on the platen), it is more desirable that a larger number of slits be provided upon each securing region so that there are multiple positions in which each securing member can be attached. The head pad 110 shown in FIG. 2 includes ten slits in each securing region, although those of skill in the art will understand that the number of slits 140 can be varied without changing the nature of the invention.

By providing a greater number of positions to which the members 120 can be attached to the platen 150, the system can accommodate a greater variety of sizes of patient's heads with the same head pad 110. This also allows a particular member to be moved from one slit 140 to another in order to more effectively secure a medical device in position upon a patient.

The head support 130 is disposed on top of the rectangular portion of the platen 150. The head support forms a contoured surface that will support the head of the patient upon whom the endo-tracheal tube is being secured. The head support 130 is desirably somewhat pliant, so as to provide some cushioning to the head of the patient. The head support 130 comprises a generally rectangular foam body when seen from above (see FIG. 3), with a generally flat bottom surface. The head support is generally dimensioned so as to fit upon the rectangular region of the platen 150, but not to extend onto the securing regions 160 of the platen.

The thickness of the head support 130 can vary, and in particular can be contoured so as to provide effective support for the head and neck of a medical patient with the back of the head upon the head support and facing upwardly away from the platen 150. This can be accomplished by contouring the head pad 130 such that the region of the support located under the neck of the patient is thicker than the region under the head. In addition, the central region of the pad can be thinner than the sides so as to provide some lateral support for the head of the patient and to prevent the head from rolling to either side and possibly dislodging the endo-tracheal tube from its proper position. In addition, the thicker neck support region also prevents the head from rocking forward with the chin moving toward the chest. This motion can cause undesirable compression of the cervical vertebrae, as well as resulting in crimping or undesirable motion of the endo-tracheal tube within the throat of the patient.

The platen 150 can be formed by injection molding from plastic or another suitable material. The head support 130 can be formed from foam or some other pliant material. The head support 130 can be attached to the platen 150 by a layer of adhesive disposed upon the upper surface of the rectangular portion of the platen. The flat bottom surface of the head support can then be placed upon this adhesive to secure the pad in position upon the platen.

The head support 130 and platen 150 can both be formed in the successive stages of the molding process and secured via adhesive, or they can be manufactured separately and assembled afterward. In addition, it can be desirable in certain applications for the head pad 110 to be disposable, in which case, materials of lesser durability can be used for the platen 150 and head support 130.

SECURING MEMBERS

Figure 6:
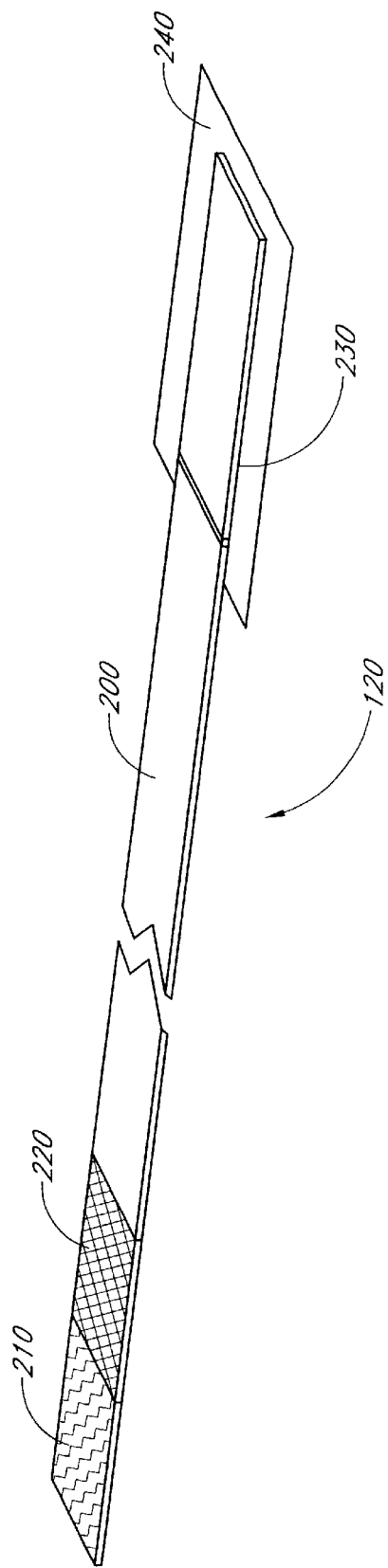
FIG. 6 illustrates a securing member of the securement system of FIG. 2.

As shown in FIG. 6, one preferred securing member 120 for use with the head pad 110 described above comprises an elongated flexible strip 200 of material which resists tearing. A variety of textiles can be used, such as a woven cotton-based textile. Woven plastic can also form a suitable material for the securing member. The member 120 is desirably long enough at least to reach from the edge of the head pad to about the mouth of the patient. The member 120 should also have enough additional length to allow it to be adjusted as necessary, as will be discussed below. This length can desirably be between about 10 and 20 inches in total length, depending upon the application.

One end of the securing member is desirably formed with hook and loop fastener material (e.g., Velcro®) disposed along one surface of the member. This can be seen in FIG. 6. For example, the end of the member can have the hook portion 210 of the fastener disposed upon the last portion of one surface, with the loop portion 220 disposed upon the adjacent portion of the same surface. The total size of the portion covered with hook and loop material can desirably be between 3 and 6 inches.

Figure 7:
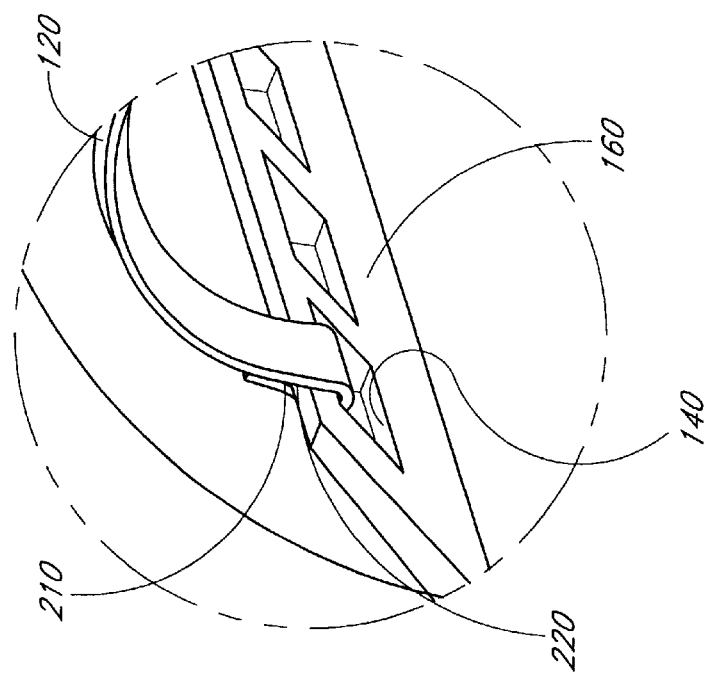
FIG. 7 is an enlarged view of the indicated portion of FIG. 2.

This end of the member 120 is used to attach the securing member to the head pad 110. The end of the member 120 with the hook and loop fastener is inserted through one of the slits 140 or holes of the securing region 160 of the head pad 110. Once inserted through, the member is folded around the edge of the securing region such that the hook portion 210 of the fastener is placed into contact with the loop portion 220 of the fastener on the end of the member. When the hooks and loops engage each other, the member 120 is now secured to the edge of the head pad 110, as shown in FIG. 7, which is an enlarged view of the circled region of FIG. 2.

The length of the free end of the member 120 can be adjusted by altering the location along the length of the hook and loop fastener at which the member wraps around the edge of the securing region 160 of the head pad 110. By pulling the hook and loop portions apart from one another, the member 120 is free to be slid through the slit of the head pad 110. Once it is pulled to the desired position, the hook portion 210 and loop portion 220 are brought together again and the member is now secured in the new position upon the head pad 110.

In order to provide a greater degree of adjustment of the overall free length of the member 120 which extends away from the slit 140 of the head pad 110, the length of the loop portion 220 of the hook and loop fastener can be extended along the member 120 away from the end with the hook portion 210. This provides a greater range of positions along the length along the member 120 to which the hook portion 210 can be secured via the loop portion 220. In particular, with a greater length of the member 120 over which the loop portion 220 extends, the member can be adjusted into a shorter overall length by securing the hook portion 210 to the loop portion 220.

The end of the member 120 without the hook and loop fastener includes a layer of adhesive 230 disposed on one side of the member. The portion of the member which has the adhesive coating is desirably between 1 and 4 inches long. This portion of the member is initially covered with a release layer 240. The release layer can comprise a paper or plastic layer which is placed over the adhesive region 230 to prevent inadvertent contact with the adhesive prior to attachment of the member 120 to the endo-tracheal tube 10 or adaptor 50.

Prior to use, the release layer 240 is peeled off of the end of the member, and the adhesive region 230 of the member 120 can then be wrapped around the endo-tracheal tube 10, or otherwise placed in contact with the tube 10 or its adaptor 50 in order to attach the tube or adaptor to the securing member 120. This process can be performed for as many or few of the members as is necessary to properly secure the tube.

Once each desired member 120 is secured to the tube 10 or adaptor 50, each member can be made snug by releasing member 120 from the head pad 110 where it is secured by the hook and loop fastener. The member can then be pulled taut to properly restrain the tub 10 in its position upon the patient. Once taut, the hook and loop fastener can be used as described above to secure the member 120 at its new length to hold this taut position.

ATTACHABLE FASTENERS

A variation upon the system described above for securing endo-tracheal tubes to a medical patient replaces the adhesive region 230 at the end of the member 120 with a different structure for fastening or connecting the end of the member to the endo-tracheal tube 10 or its adaptor 50. One such system uses a hook and an eyelet. In order to use such a system, appropriate eyelets or other rings, receptacles or apertures can be disposed upon the tube 10 or adaptor 50. Additionally, in some applications, it can be desirable to create apertures which are formed through the wall of the endo-tracheal tube and to which the members can be attached.

One technique for accomplishing this is to manufacture endo-tracheal tubes that have eyelets already molded on the tube. The eyelets are preferably located such that they are disposed at a location convenient for one or more of the members 120 to be attached to them. Another technique is to provide a separate set of attachable eyelets that can be quickly attached to a tube or adaptor when they are needed.

Figure 8:
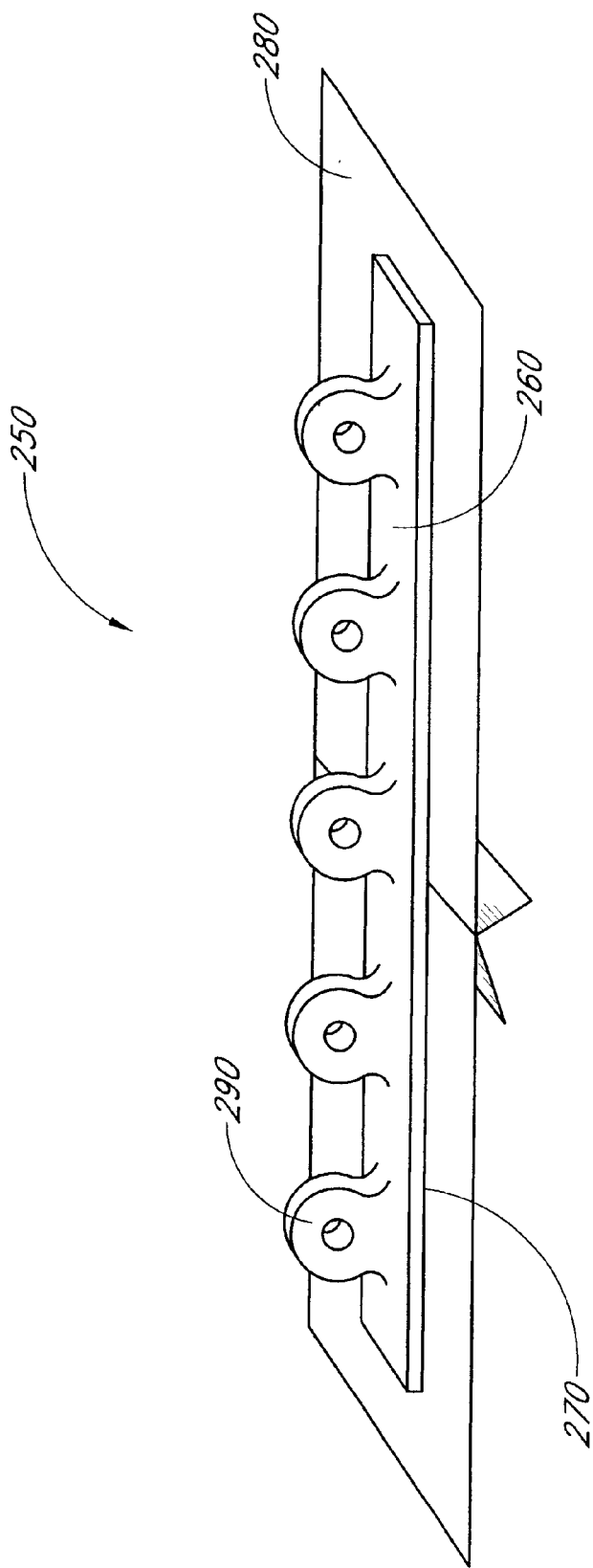
FIG. 8 illustrates an attachable fastener in accordance with another preferred embodiment of the present invention.

One set of attachable eyelets 250 for use with the present securement system is shown in FIG. 8. As can be seen, the attachable component comprises an elongated plastic or woven strip 260. One side of the strip is covered with an adhesive layer 270, and the adhesive layer is covered with a release liner 280 until it is ready for use in order to prevent unintentional adhesion. If desired, the release liner 280 can be split so that it can be peeled off in two sections, as shown in FIG. 8. The opposite side of the strip 260 includes a number of plastic or woven rings or eyelets 290 through which hooks from the securing members 120 can be inserted (described below).

The strip 250 shown in FIG. 8 shows the eyelets 290 arranged such that the axis of the opening of the eyelet 290 is normal to the long axis of the strip 260. However, those of skill in the art will recognize that the axis of the openings in the eyelets 290 need not be oriented in this direction. The eyelets 290 could also be oriented perpendicular to the arrangement shown so that the axis of all the eyelets was substantially aligned and was parallel to the long axis of the strip 260. Those of skill in the art will recognize that various angled arrangements for the eyelets are also possible, and that the axis of each eyelet need not be oriented in the same direction.

In order to use the eyelet strip 250, the adhesive layer 270 is exposed by peeling the release layer 280 from the strip 260. Once this region is exposed, the adhesive layer 270 of the strip 120 is then wrapped around the endo tracheal tube 10. This results in the configuration shown in FIG. 9. Once the eyelet strip 250 is mounted upon the endo-tracheal tube 10, securing members 120 can be used to connect the eyelets 290 to the head pad 110 of the securement system.

Those of skill in the art will also recognize that the fastener disposed upon the attachable strip need not be eyelets designed for use with hooks. Other arrangements include but are not limited to: snaps, clips, or such other fasteners as are known to those of skill in the art.

Figure 9:
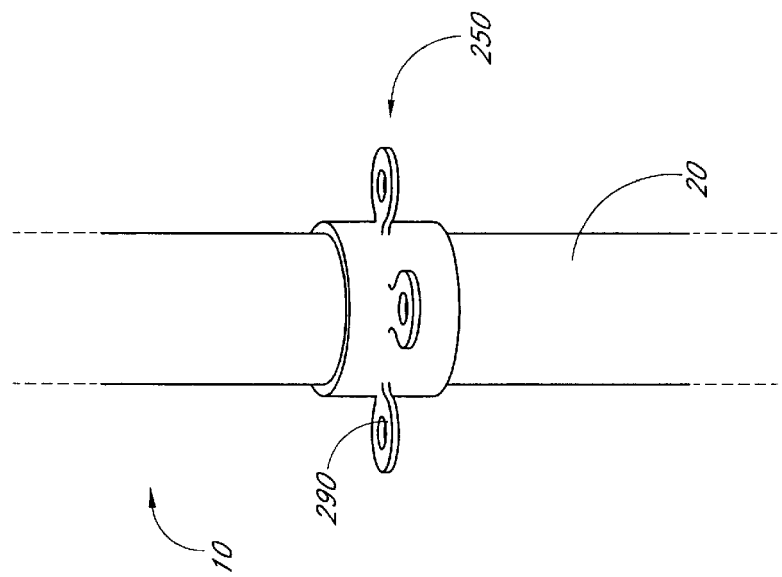
FIG. 9 illustrates the attachable fastener of FIG. 8 in use upon an endo-tracheal tube.

In addition to the system described above, other designs for attachable fasteners are also possible. For instance, rather than having the fastener elements disposed upon a flat strip 260 which is then wrapped around the endo-tracheal tube, it is possible to have the attachable fastener pre-formed into a short cylindrical piece or ring. The fasteners can be disposed upon this cylinder so that they form a configuration similar to that of the attachable eyelet strip 250 once attached to a tube, as shown in FIG. 9. Desirably, the cylinder is slit along its length at a location about its circumference to allow the cylinder to be flexed into a less curved position and then placed into position around the tube.

This ring-style attachable fastener can be formed of a flexible material which tends to hold its shape, but which can be flexed or bent by a medical practitioner without fracturing. The desired shape for such a fastener is substantially similar to the shape of the strip-style attachable fastener shown in FIG. 9 once it has been attached to the tube. The cylinder is placed in the desired position longitudinally upon the tube, and then it is released and allowed to return toward its original shape. In returning to its original unflexed shape around the tube, the cylinder can grip the outer surface of the tube even without the use of adhesive. Such an arrangement can be advantageous in circumstances where it becomes desirable to reposition the fasteners upon the tube. In order to improve traction between the cylinder and the tube 10, the inner surface of the tube can be roughened, or otherwise treated with a high friction coating to provide a better grip between the tube and cylinder. This will help inhibit any undesired motion of the cylinder upon the tube 10 once the cylinder is in position.

Other variations of fasteners which can be attached or disposed upon the tube or adaptor include flexible clamps to clamp fasteners around the outer surface of the endo-tracheal tube. Those of skill in the art will recognize that there are a variety of techniques which are applicable for attaching fastening elements to the endo-tracheal tube.

TUBE ADAPTOR

Figure 10:
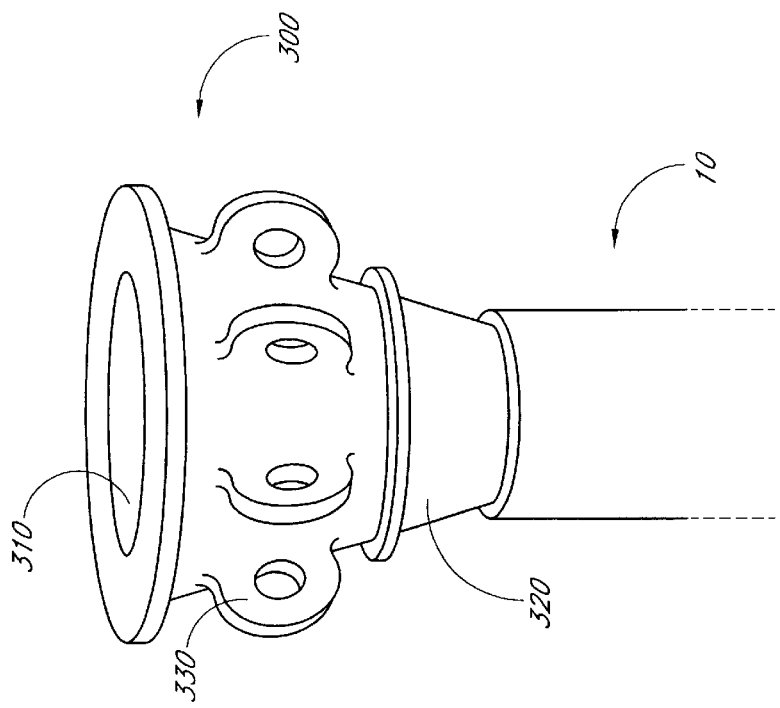
FIG. 10 illustrates a tube adaptor having eyelets in accordance with another preferred embodiment of the present invention.

Another technique for providing appropriate fasteners for the securing members is to provide fasteners, connectors or other anchoring receptacles, such as holes or eyelets, upon the endo-tracheal tube adaptor. For example, as shown in FIG. 10, eyelets can be disposed upon the tube adaptor for use with hooks disposed upon the securing members. As shown in FIG. 10, the tube adaptor 300 comprises a generally tubular plastic piece with a generally tapering diameter to its inner lumen 310. One end of the adaptor 300 is provided with a tapered region 320 which can be inserted into the end of an endo-tracheal tube 10, while the other end can be connected to an external tube of some kind, for example, the end of a ventilator.

As shown in FIG. 10, the adaptor 300 also can include suitable anchors for attachment to the securing members 120 of the endo-tracheal securing system 100. A number of eyelets 330 are shown disposed around the circumference of the central portion of the tube adaptor 300. This region of the adaptor 300 is between the end 320 of the adaptor that is inserted into the endo-tracheal tube 10, and the end of the adaptor 300 that attaches to an external medical tube or device.

As can be seen in FIG. 10, the eyelets 330 can desirably be disposed such that each of the axes of the holes of the eyelets are roughly tangential to the circumference of the tube adaptor 300 at the point where the eyelet is attached to the adaptor. Those of skill in the art will recognize that these eyelets can also be disposed such that the axes of the eyelets are generally all parallel to the axis of the adaptor 300 itself. In general, the eyelets 330 can be disposed in any arrangement which is suitable for cooperating with the hooks of the securing members 120. For instance, any of the orientations discussed with respect to the attachable eyelet strip 250 above can also be used here.

The number of eyelets 330 or other fasteners disposed on the adaptor 300 can vary, but is preferably at least equal to the number of members 120 which will be fastened to the adaptor 300. As is discussed above with respect to the attachable eyelets, a variety of different fasteners can be disposed upon the adaptor other than eyelets without altering the nature of the system described.

SECURING MEMBERS WITH FASTENERS

Figure 11:
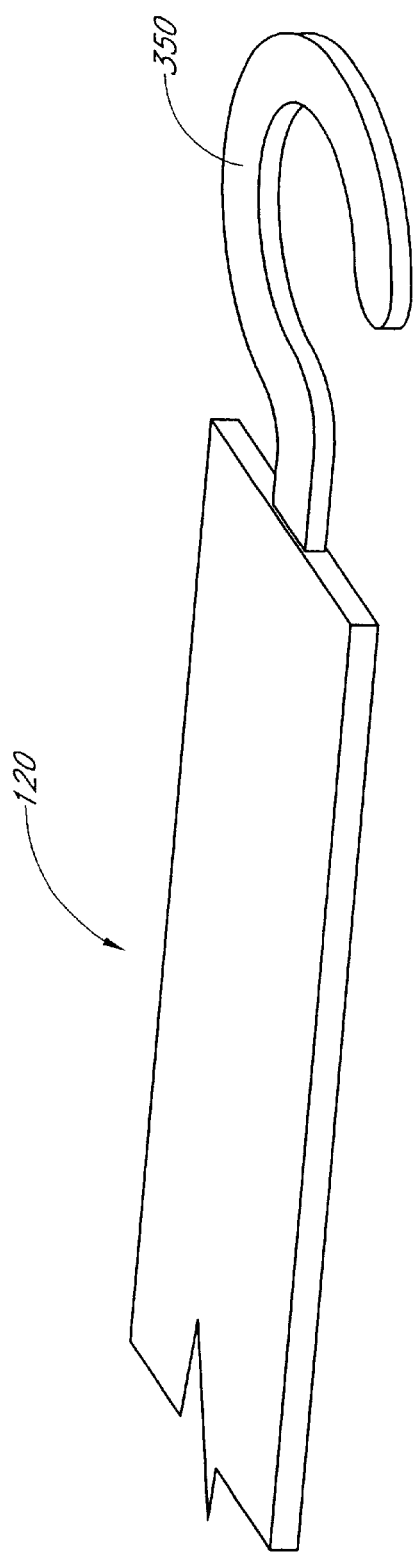
FIG. 11 illustrates a securing member in accordance with another preferred embodiment of the present invention.

In order to work with eyelets as shown with the attachable eyelet strip 250 or the tube adaptor 300 described above, a variation upon the securing members 120 described above can be used. One example of an appropriate member suitable for use with the eyelets 290, 330 described above is shown in FIG. 11.

The general structure and configuration of the securing member 120 is substantially the same as that shown in FIG. 6 and described above. The end of the member 120 which is attached to the head pad 110 is configured with hook and loop fasteners, and can be adjusted or released as described above. However, rather than an adhesive region upon the end of the securing member not attached to the head pad 110, a hook 350 is attached to the member 120. The hook 350 is dimensioned and configured to be inserted through an eyelet or other aperture disposed upon the tub 10 or adaptor 50, 300. These eyelets or apertures can be part of either an attachable eyelet strip 250 or a cylindrical ring with eyelets, as described above. The eyelets or apertures can also be integrally formed with the tube 10 or the tube adaptor 300.

When securing an endo-tracheal tube using the hooks 350 of these securing members in combination with either an attachable eyelet strip 250 or with an adaptor 300 having eyelets, the hooks 350 are placed through the eyelets 290, 330, and then the members 120 are made snug as described above by releasing the loop and hook fastener at the end of each member, pulling the member taut, and then resecuring the loop and hook fasteners to hold the member in this taut position.

Those of skill in the art will also recognize that if a fastener system other than a hook and eyelet combination is used that the hook can desirably be replaced by the appropriate portion of the fastener. For instance, if snaps are to be used, a snap receptacle can be disposed upon the securing member, and a snap protrusion can be disposed upon the attachable strip or adaptor.

OPERATION

Figure 12:
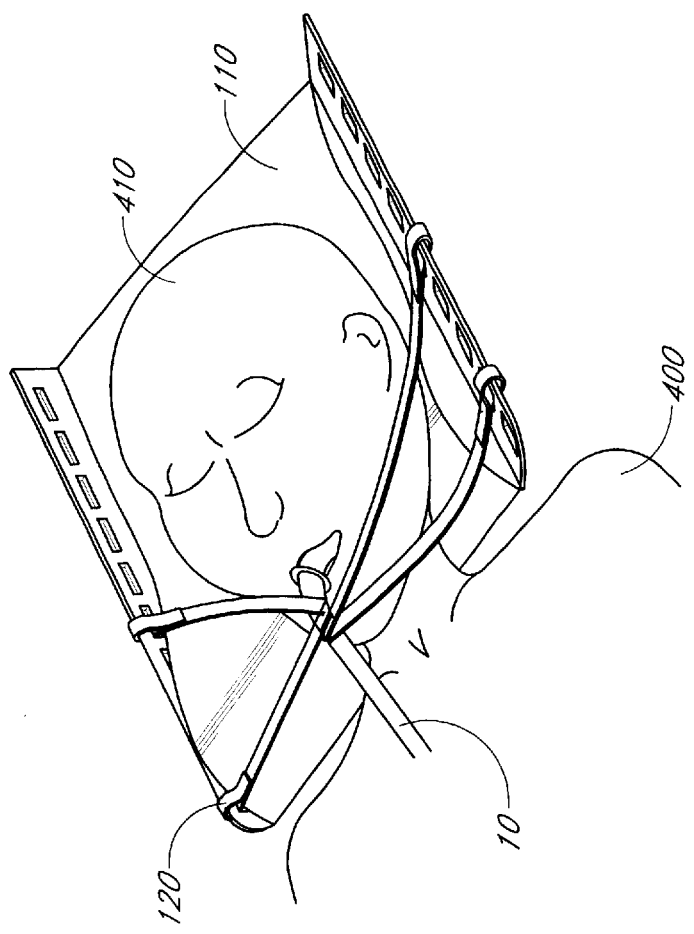
FIG. 12 illustrates the use of the securement system of FIG. 2 in use upon a patient.

As illustrated in FIG. 12, a medical attendant can secure an endo-tracheal tube 10 (or other medical article) to a patient 400 using the above-described securement system 100 (or a readily apparent modification thereof). The medical attendant places the head 410 of the patient 400 upon the head pad 110 such that the neck of the patient is properly supported by the head pad 110 and the head 410 is not rotated toward either side of the patient's body. This can be performed either before or after the patient is intubated.

If the securing members 120 are not already attached to the head pad 110, they can each be threaded through one of the slits 140 of the head pad 110, and then secured in position via the hook and loop fastener on each member 120. The securing members 120 can also be moved from one slit 140 to another in order to provide more appropriate anchoring points for the securement of the tube 10 upon the patient 400. For example, if the patient is young and has a smaller head, the position of the tube can be relatively closer to the end of the head pad than if the patient were fully grown. In order to accommodate this, it can be desirable to attach two of the members 120 to the head pad 110 at a position which is located partway down the length of the head pad, rather than closer to the end of the head pad. By providing multiple slits 140 on each side of the head pad 110, the system 100 can accommodate a wide variety of sizes of patients.

Once the members 120 are secured properly to the head pad 110, each member is attached to the endo-tracheal tube 10 or its adaptor. This can be accomplished via one of the techniques described above and will vary depending upon the type of fasteners provided upon the tube and members. For instance, if adhesive strips as shown in FIG. 6 are provided upon the securing members, the release liner 240 is removed and the adhesive is attached directly to the tube 10 or adaptor, as shown in FIG. 12.

If eyelets or snaps are disposed upon the tube or adaptor, then members with hooks or snap receptacles can be used to connect the members to the tube 10 or adaptor 50. In the case where no fastener is disposed upon the tube 10 or adaptor 50, an attachable fastener such as the attachable eyelet strip 250 described above can be attached to the tube 10 or adaptor as desired.

The connection between the head pad 110 and the tube 10 can be made secure by releasing the hook and loop side of each member 120 and pulling it snug between the head pad 110 and the tube 10. Once taut, the hook and loop fastener portions 210, 220 are resecured. Once all the members 120 are snug, undesirable motion of the endo-tracheal tube 10 is inhibited.

Once secured in the above manner, the oral cavity of the patient 400 remains accessible to the medical practitioner. This allows for oral care such as suction to be performed without the need to remove the tube 10 from the patient 400, or to untape or otherwise undo the securement of the tube to the patient.

The described system allows a medical practitioner to adjust the position in which the tube 10 is secured if any adjustment becomes necessary. For example, if the tube's position must be adjusted upon the patient (e.g., if the patient has shifted, or it has been determined the tube is placed too deeply or too shallowly within the patient), this can be accomplished by the same procedure described above for making the members snug. The hook and loop fasteners of each member 120 are released, the tube 10 is repositioned, and then the members 120 are made snug and resecured with the hook and loop fastener.

Similarly, if there is a need to rapidly remove the tube from a patient, the members 120 can be quickly released from the patient 400 by either removing the hooks or other fasteners from the eyelets, or in the case where an adhesive attachment is used between the members and the tube, the members 120 themselves can be quickly released from the head pad 110 by pulling the hook and loop fasteners open. This allows the members 120 to be removed from the head pad 110, and the entire tube 10 with the members still attached to be removed from the patient 400.

VARIATIONS

In addition to the variations described above, it is also possible to configure the system to use hook and eyelet pairs where the hooks are disposed not on the securing members, but on the medical articles to be secured instead. The appropriate eyelets can then be located on the free end of the securing members. In this way, the same securing operation as described above with respect to hook and eyelet fasteners can be used.

Figure 15:
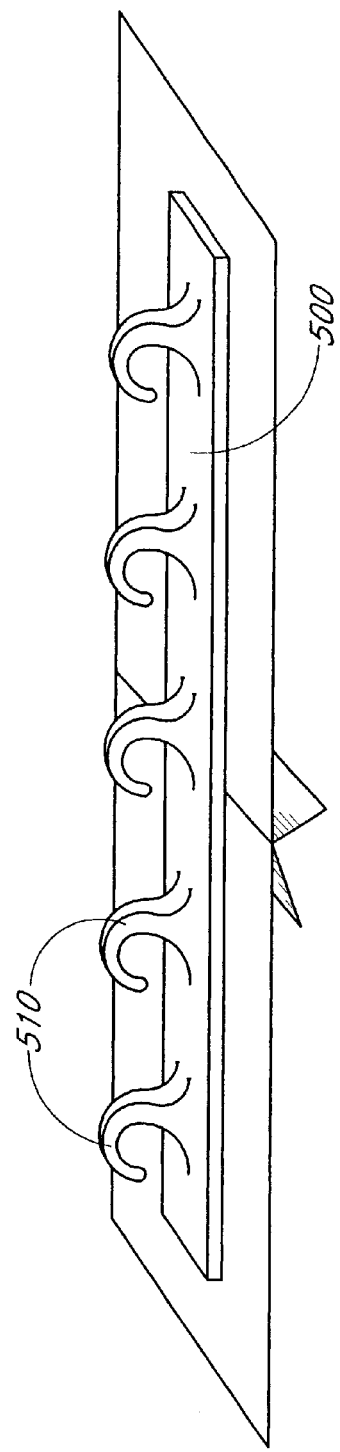
FIG. 15 illustrates an attachable fastener having hooks in accordance with another preferred embodiment of the present invention.

By placing the hooks in a fixed position upon the medical articles to be secured, such as the endo-tracheal tube or its adaptor, the free ends of the securing members need only include an eyelet or other aperture. This can simplify the manufacture of the members, and can also present certain safety advantages. Examples of such variations including these features are illustrated in FIGS. 13 to 15 and described below.

Figure 13:
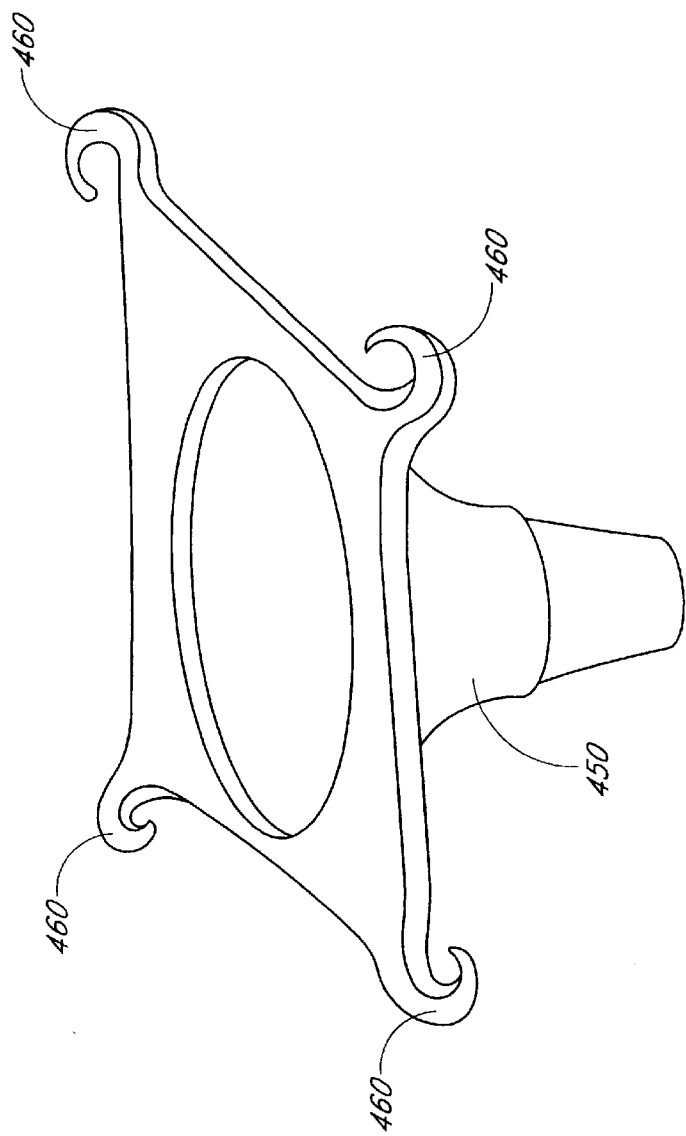
FIG. 13 illustrates a tube adaptor having hooks in accordance with another preferred embodiment of the present invention.

FIG. 13 illustrates an exemplary endo-tracheal tube adaptor 450 that includes hooks 460 suitable for use with securing members 120 that include eyelets or other apertures. If such an adaptor 450 is used with an endo-tracheal tube 10, the securing members 120 of the securing system can be attached to the hooks 460 on the adaptor 450.

An appropriate securing member 120 for use with such hooks 460 is illustrated in FIG. 14. The free end of the securing member 120 is illustrated, and includes an opening 480, such as a hole or aperture, in the end of the member 120. The opening 480 is dimensioned to accept the hooks 460 on the adaptor 450 or other medical article to be secured. The opening on the member 120 can simply be a hole which is disposed near the end of the member, or can include a grommet or other support for the opening which helps inhibit any stretching or tearing of the member due to the pressure exerted between the hook 460 and the member 120.

As illustrated in FIG. 14A, the securing member 120 can also include a plurality of openings 480 in order to allow for simpler or more rapid adjustment of the connection between the head pad 110 and the medical article being secured. A member 120 including four openings is illustrated, but it will be understood by those of skill in the art that the number of openings 480 can be either greater or less than four without altering the nature of the system described.

Although the adaptor 450 shown in FIG. 13 has four hooks 460 disposed around the upper lip of the adaptor, the adaptor can also be configured with either a greater or lesser number of hooks. The position and direction of the hooks 460 can also be altered from that shown in the configuration of FIG. 13.

For instance, FIG. 13 shows the hooks 460 disposed radially about the upper surface of the adaptor. However, it is also possible to use an adaptor on which the hooks 460 are disposed from opposite sides of the upper surface of the adaptor, for example, two hooks extending from each of a pair of opposite lateral sides of the adaptor. Other possible arrangements include providing a greater number of hooks, for example six hooks disposed radially about the adaptor. Such an arrangement can be particularly well suited to adaptors which have a hexagonal upper lip. It is also possible to use an adaptor upon which the hooks are positioned at a location below the upper surface, similar to the position shown for the eyelets 330 in FIG. 10.

As described above with respect to the eyelet on the tube or adaptor, the individual hooks can be disposed such that the curved portion of the hooks extend in a plane normal to the axis of the tube, rather than extending in a plane parallel to the axis of the tube (as shown in FIG. 13).

In addition to the illustrated tube adaptor 450 with hooks 460 shown in FIG. 13, the securing members 120 of FIGS. 14 and 14A can also be used with an endo-tracheal or other tube which is integrally formed to include one or more hooks. These can be disposed in substantially the same positions and arrangements as the eyelets 290 are disposed upon the tube in FIG. 9. Similarly to what is described above, the hooks need not extend in a plane strictly normal to the axis of the tube, but can be disposed in a plane parallel to the axis of the tube.

For use with tubes 10 that do not have hooks molded upon them, an attachable fastener 500 with hooks 510 can be provided. Such an attachable fastener, as shown in FIG. 15, is substantially as described above with reference to FIG. 8. However, rather than including one or more eyelets disposed along the fastener, one or more hooks 510 are provided. Although the attachable fastener 500 shown in FIG. 15 has hooks which extend along the length of the fastener, it will be understood that the hooks can extend across the width of the fastener without altering the nature of the system described.

The various embodiments of the securement systems described above in accordance with the present invention thus provide a means to secure an endo-tracheal tube or other medical article to a patient releasably. The tube can be adjusted without removing the entire securement assembly, and without the need for use of additional tape to resecure the tube once it is properly repositioned. The securement system inhibits both inward and outward migration of the tube within the patient, and allows for access to the oral cavity of the patient in order to allow propriate mouth care to take place.

Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or Furthermnore, the skilled artisan will recognize the interchangeability of various features from different embodiments. In addition to the variations described herein, other known equivalents for each feature can be mixed and matched by one of ordinary skill in this is to construct securement systems and techniques in accordance with principles of the present invention.

Although this invention has been disclosed in the context of certain preferred embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

What is claimed is:

1. An endo-tracheal tube securement device comprising:
   a head pad having a support and a platen, the platen comprising a generally flat rectangular member having a central region and at least a pair of securing regions, one of the pair of securing regions extending from each lateral side of the platen, each securing region having a plurality of openings, and the support coupled to an upper surface of the platen such that the openings of the pair of securing regions are accessible to each lateral side of the support; and
   a plurality of securing members, each securing member having a first end and a second end, the first end having a hook region upon which the hooks of a hook and loop fastener are disposed and a loop region upon which the loops of a hook and loop fastener are disposed, and the second end having a fastener configured to attach the member to an endo-tracheal tube to be secured in position upon the head of a patient, each of the plurality of securing members configured to be attached to the head pad by passing the first end of the member through one of the openings of the head pad and then attaching the hook region of the member to the loop region of the member to secure the member to the head pad.

2. The endo-tracheal tine securement device of claim 1 wherein the fastener of the second end of the securing member comprises an adhesive layer disposed upon one side of the second end of the securing member.

3. The endo-tracheal tine securement device of claim 2 wherein the adhesive layer of the securing member is covered by a removable release liner.

4. The endo-tracheal tine securement device of claim 1 wherein the fastener of the second end of the securing member comprises a hook configured to cooperate with an aperture of the endo-tracheal tube.

5. The endo-tracheal tine securement device of claim 1 wherein the fastener of the second end of the securing member comprises an aperture configured to be secured to a hook of the endo-tracheal tube.

6. The endo-tracheal tine securement device of claim 5 wherein the second end of the securing member comprises a plurality of additional apertures at different positions along the second end of the member.

7. The endo-tracheal tine securement device of claim 1 wherein the length of at least one of the plurality of securing members may be adjusted by adjusting the position upon the loop region of the member to which the hook region of the member is attached.

8. A medical tube securement system comprising:
   a medical tube to be secured in position upon the head of a patient;
   a head pad having a support and a platen, the platen comprising a generally flat rectangular member having a central region and at least a pair of securing regions, one of the pair of securing regions extending from each lateral side of the platen, each securing region having a plurality of openings formed in it; and
   a plurality of securing members, each securing member having a first end and a second end, the first end having a hook region upon which the hooks of a hook and loop fastener are disposed and a loop region upon which the loops of a hook and loop fastener are disposed, and the second end having a fastener configured to attach the member to the medical tube, each of the plurality of securing members configured to be attached to the head pad by passing the first end of the member through one of the openings of the head pad and then attaching the hook region of the member to the loop region of the member to secure the member to the head pad.

9. The medical tube securement system of claim 8 wherein the fastener of the second end of the securing member comprises an adhesive layer disposed upon one side of the second end of the securing member.

10. The medical tube securement system of claim 9 wherein the adhesive layer of the securing member is covered by a removable release liner.

11. The medical tube securement system of claim 8 wherein the medical tube further comprises at least one aperture and the fastener of the second end of the securing member comprises a hook configured to cooperate with the aperture of the medical tube.

12. The medical tube securement system of claim 8 wherein the medical tube further comprises a hook and the fastener of the second end of the securing member comprises an aperture configured to be secured to the hook of the medical tube.

13. The medical tube securement system of claim 12 wherein the second end of the securing member comprises a plurality of additional apertures at different positions along the second end of the member.

14. A system for securing a medical article to the head of a patient comprising:
   a head pad having a support and a platen, the platen comprising a generally flat rectangular member having a central region and at least a pair of securing regions, one of the pair of securing regions extending from each lateral side of the platen, each securing region having a plurality of openings formed in it;
   a plurality of securing members, each securing member having a first end and a second end, the first end having a hook region upon which the hooks of a hook and loop fastener are disposed and a loop region upon which the loops of a hook and loop fastener are disposed, and the second end having a first fastener element, each of the plurality of securing members configured to be attached to the head pad by passing the first end of the member through one of the openings of the head pad and then attaching the hook region of the member to the loop region of the member to secure the member to the head pad; and
   an attachable fastener unit comprising a support member and at least one second fastener element disposed upon the support member, the support member configured to be attached to the medical article and the second fastener element configured to cooperate with the first fastener element to attach a securing member to the attachable fastener unit.

15. The system of claim 14 wherein the support member of the attachable fastener unit comprises a flexible elongated strip having an adhesive for attaching the fastener unit to the medical article, the adhesive being disposed upon one side of the strip and the adhesive being covered by a removable release liner, and wherein the second fastener element is disposed upon the opposite side of the strip from the adhesive.

16. The system of claim 14 wherein the support member of the attachable fastener unit comprises a flexible, generally cylindrical body having a opening along the length of the body to allow the body to be flexed sufficiently to allow it to be inserted around the body of the medical article, the second fastener element being disposed upon the outside of the cylindrical body.

17. A method for securing a medical tube upon the head of a patient, comprising:

providing a head pad having a support and a platen, the platen comprising a generally flat rectangular member having a central region and a pair of securing regions, one of the pair of securing regions extending from each lateral side of the platen, each securing region having a plurality of openings formed in it;

placing the head of the patient upon the support of the head pad;

positioning a medical tube upon the head of the patient;

providing a plurality of securing members, each securing member comprising a flat elongated flexible strip having a first end and a second end, the first end having a hook region upon which the hooks of a hook and loop fastener are disposed and a loop region upon which the loops of a hook and loop fastener are disposed, and the second end having a first fastener element;

attaching the first fastener element of each of the securing members to the medical tube; and making each of the securement members snug between the head pad and the medical tube by passing the first end of the member through one of the openings of the head pad and then attaching the hook region of the member to the loop region of the member in a position such that the member is taut.

\* \* \* \* \*

UNITED STATES PATENT AND TRADEMARK OFFICE
CERTIFICATE OF CORRECTION

PATENT NO. : 6,796,310 B2
DATED : September 28, 2004
INVENTOR(S) : Steven F. Bierman It is certified that error appears in the above-identified patent and that said Letters Patent is hereby corrected as shown below:

Column 2,
Line 41, after "another" delete "node" and insert -- mode --.
Line 63, after "The" delete "secuing" and insert -- securing --.

Column 12,
Line 49, after "allow" delete "propriate" and insert -- appropriate --.
Line 58, after "taught or" insert -- suggested herein. --.
Line 59, delete "Furthermnore" and insert -- Furthermore --.
Line 63, after "this" delete "is" and insert -- art --.

Column 13,
Lines 33, 37, 40, 44, 48 and 52, after "endo-tracheal" delete "tine" and insert -- tube --.

Signed and Sealed this

Fourth Day of April, 2006

JON W. DUDAS
*Director of the United States Patent and Trademark Office*